United States Patent [19]

House

[11] 3,965,159

[45] June 22, 1976

[54] CARBOXYDISULFOSUCCINATES

[75] Inventor: Ralph House, El Sobrante, Calif.

[73] Assignee: Chevron Research Company, San Francisco, Calif.

[22] Filed: Jan. 2, 1975

[21] Appl. No.: 538,042

[52] U.S. Cl. .......................... 260/513 R; 252/89 R; 252/95; 252/530; 252/549; 252/DIG. 15
[51] Int. Cl.² ............... C07C 143/04; C07C 143/12
[58] Field of Search .................... 260/513 R, 513 T

[56] References Cited
UNITED STATES PATENTS

| | | | |
|---|---|---|---|
| 2,345,041 | 3/1944 | Ericks et al. | 260/485 P |
| 2,448,831 | 9/1948 | Roberts et al. | 260/513 R |
| 3,706,771 | 12/1972 | Kremers et al. | 260/513 R |

OTHER PUBLICATIONS

Backer et al., Rec. Traveanx Chim., 49, 735, (1930).

*Primary Examiner*—James O. Thomas, Jr.
*Assistant Examiner*—Nicky Chan
*Attorney, Agent, or Firm*—G. F. Magdeburger; John Stoner, Jr.; W. Keith Turner

[57] ABSTRACT

Carboxydisulfosuccinates useful as detergent builders are novel compounds prepared by addition of $CO_2$ to disulfosuccinate.

3 Claims, No Drawings

CARBOXYDISULFOSUCCINATES

BACKGROUND OF THE INVENTION

1. Field of the Invention

This application is concerned with a novel polyacidic compound and a process for producing it.

2. Description of the Prior Art

Compounds such as disulfosuccinic acid and its salts have been suggested as building materials in heavy-duty detergent compositions. These compounds are effective in boosting the detergent effectiveness of various detergent-active materials, including anionic, cationic, nonionic and zwitterionic materials.

SUMMARY OF THE INVENTION

Novel carboxysulfoxy compounds useful as detergent builders are provided. The compounds, carboxydisulfosuccinate and salts thereof, have the following formula:

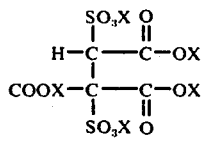

in which X is H or an alkali metal, alkaline earth metal or ammonium cation.

The compounds are prepared by reacting a salt of disulfosuccinic acid with at least a molar amount of carbon dioxide at elevated temperature and pressure for a period of from about ½ to 12 hours, preferably from about 1 to 6 hours.

The temperature of the reaction is in the range of from about 110°C to 200°C, preferably from about 120°C to 180°C.

The pressure maintained during the reaction will be between about 1.2 to 16 atmospheres, preferably from about 2 to 12 atmospheres.

The carbon dioxide may be introduced in gaseous form or by any convenient means of generating carbon dioxide in situ. For example, a bicarbonate or carbonate may be employed. Suitable compounds thus include the alkali metal and ammonium carbonates. When the salts are employed, they are used in molar ratios of from about 1:5 to 5:1, preferably 1.1:1 to 3:1 relative to the disulfosuccinate.

The preparation of the compound of this invention is illustrated in the following example, which is non-limiting.

EXAMPLE

An aqueous solution of tetraamonium disulfosuccinate was heated with ammonium carbonate for a period of 3 hours at a temperature of 150°C. The product was subjected to a nuclear magnetic resonance (NMR) analysis in $D_2O$ containing acetic acid. Results showed a new peak at 146 H2 above the acetic acid peak in addition to the peaks corresponding to the meso and dl forms of disulfosuccinate (134 Hz and 140 Hz above the acetic acid peak). The analysis showed that from the starting 1.94 mmols of disulfosuccinic acid, the product contained 1.27 mmols of unreacted disulfosuccinic acid and 0.75 mmol of monocarboxydisulfosuccinic acid. On a weight basis, the product represents 59% unreacted material and 41% monocarboxylated product.

The compounds of this invention are useful in enhancing the detergency of anionic, cationic, nonionic and zwitterionic detergent-active materials. They are most useful with anionic detergents, particularly with the commonly used linear alkylbenzene sulfonates (LAS) which are employed in most detergent compositions.

The builders are employed in the detergent compositions in amounts of from about 5% to 75%, usually 10% to 50% by weight of the total composition.

In addition to the detergent-active and builder, the compositions will often be formulated with additional conventional detergent-actives such as anticorrosion, antiredeposition, bleaching and sequestering agents, as well as various filler materials such as the inorganic alkali metal salts such as the sulfates, carbonates, silicates or borates, etc.

While the character of this invention has been described in detail with an illustrative example, this has been done by way of illustration only and without limitation of the invention. It will be apparent to those skilled in the art that modifications and variations of the illustrative example may be made in the practice of the invention within the scope of the following claims.

I claim:

1. A compound useful as detergent builders having the formula:

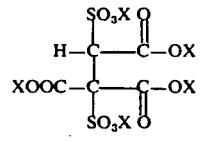

in which X is H or an alkali metal, alkaline earth metal or ammonium cation.

2. A compound of claim 1 in which X is alkali metal.

3. A compound of claim 2 in which X is sodium.

* * * * *